United States Patent [19]

Ishida et al.

[11] Patent Number: 4,781,690
[45] Date of Patent: Nov. 1, 1988

[54] GUIDING TUBE FOR MEDICAL INSTRUMENTS

[75] Inventors: Toshinobu Ishida; Yousuke Moriuchi; Tadashi Kousai, all of Fujinomiya, Japan

[73] Assignee: Terumo Kabushiki Kaisha, Tokyo, Japan

[21] Appl. No.: 25,625

[22] Filed: Mar. 13, 1987

[30] Foreign Application Priority Data

Mar. 20, 1986 [JP] Japan .................................. 61-63249

[51] Int. Cl.$^4$ ........................ A61M 5/00; A61M 25/00
[52] U.S. Cl. ..................................... 604/164; 604/280
[58] Field of Search ..................... 604/51-53, 604/158-170, 280-284

[56] References Cited

U.S. PATENT DOCUMENTS

| 3,656,479 | 4/1972 | Huggins | 604/161 |
| 3,720,210 | 3/1973 | Diettrich | 604/283 |
| 4,054,136 | 10/1977 | Zeppelin | 604/160 |
| 4,402,685 | 9/1983 | Buhler et al. | 604/164 X |

FOREIGN PATENT DOCUMENTS 0021446  1/1981  European Pat. Off. .
1381053  1/1975  United Kingdom .

OTHER PUBLICATIONS

European Search Report No. 87103779.2.

Primary Examiner—Dalton L. Truluck
Attorney, Agent, or Firm—Burns, Doane, Swecker & Mathis

[57] ABSTRACT

There is disclosed a guiding tube for introducing rod-like medical instruments such as a catheter, which can be easily split and removed from, for example, a catheter, after the catheter inserted through the guiding tube has been attached to a blood vessel. The guiding tube comprises a main body provided with a longitudinal slit and formed of a mixture of first and second materials and a stripe detachably embedded liquid-tight in the slit of the main body and formed of a third material which exhibits a good bonding to the second material, but a poor bonding to the first material.

12 Claims, 3 Drawing Sheets

GUIDING TUBE FOR MEDICAL INSTRUMENTS

BACKGROUND OF THE INVENTION (a) Field of the Invention

The present invention relates to a synthetic resin tube for guiding a rod-like medical instrument such as a catheter and a guide wire into, for example, a blood vessel and for keeping the medical instrument attached to the blood vessel.

(b) Description of Prior Art

A flexible tube of synthetic resin is generally used for guiding, for example, a catheter into a blood vessel and for keeping the catheter attached to the blood vessel. As shown in FIG. 1, a guiding tube 1 is mounted to a syringe 2 such that the tip of an inner needle 3 of the syringe 2 projects outward through the tip of the guiding tube 1. Then, the inner needle 3 is inserted into a blood vessel 4 until the tip of the guiding tube 1 is positioned within the blood vessel 4, as shown in FIG. 2. Under this condition, the inner needle 3 is withdrawn from the blood vessel 4, with the guiding tube 1 kept attached to the blood vessel 4. Further, a desired catheter 5 is inserted into the guiding tube 1 until the tip of the catheter 5 is positioned within the blood vessel 4, as shown in FIG. 3. After the catheter 5 has been attached to the blood vessel 4 as desired, it is desirable to withdraw the guiding tube 1 from the blood vessel 4 and from the catheter 5. It is sanitarily undesirable to leave the guiding tube 1 in the vessel after use. Also, the guiding tube, left unremoved after use, hinders the operation of the catheter 5. However, the presence of an enlarged portion, such as a connector 6 of the catheter, makes it quite difficult to withdraw the guiding tube 1 from the catheter 5.

Several measures have been proposed to date for withdrawing the guiding tube 1 from the catheter 5 after use. For example, it has been proposed to provide the guiding tube with a longitudinal slit to enable the guiding tube after use to be readily removed from the catheter. However, serious problems result. For example, the strength of the guiding tube is lowered, making it troublesome to operate the guiding tube. Also, the slit of the guiding tube is likely to expand when the catheter is inserted through the guiding tube into a blood vessel, leading to a leakage of blood. To overcome this problem, unavoidably the slit must be made narrow, with the result that removal of the guiding tube from the catheter is difficult.

Japanese Patent Disclosure (Kokai) 56-11069 proposes another measure. Specifically, it is proposed that a guiding tube is provided with a pair of linear bodies extending along the length of the guiding tube and positioned opposite to each other in the radial direction of the guiding tube. The linear body is formed of a plastic material foreign to the material forming the main body of the guiding tube. Also, the proximal end portion of the guiding tube, which is joined to the inner needle hub, of the guiding tube is provided with a pair of slits aligned with the linear bodies. After a catheter or the like, inserted through the guiding tube, has been attached to a blood vessel, the proximal end portions of the guiding tube are pulled outward in opposite directions. As a result, the guiding tube after use is split into two parts along the linear bodies. Of course, the slits formed in the proximal end portion of the guiding tube facilitate the splitting. In this proposal, however, the linear body tends to crack during post production treatments, such as cutting or edge-processing of the guiding tube, or during transport or the like of the product guiding tube, with the result that is used leakage of blood is likely to take place so as to make the guiding tube unsuitable for use.

SUMMARY OF THE INVENTION

An object of the present invention is to provide a guiding tube for rod-like medical instruments such as a catheter, which is free from accidental splitting or cracking during post manufacture treatment of the guiding tube or during handling of the guiding tube. Another object of this invention is to provide a guiding tube which can be easily removed from, for example, a catheter after the catheter, inserted through the guiding tube, has been attached to a blood vessel.

According to the present invention, there is provided a tube for guiding rod-like medical instruments into a living body, comprising:

a main body provided with a longitudinal slit and formed of a mixture of first and second materials; and a stripe-shaped member (referred to hereinafter as "stripe") embedded liquid-tight in the slit of the main body and formed of a third material;

said first material being substantially incapable of bonding to the third material, and said second material exhibiting a high bonding strength to the third material such that the stripe can be readily detached from the slit of the main body by application of a predetermined force to allow the guiding tube to be removed from the medical instrument after introduction of the medical instrument through the guiding tube.

The first material used in the guiding tube of the present invention is selected from polyolefin resins such as high-density polyethylene, polypropylene and ethylene-propylene copolymer. The second material is prepared by modifying the first material polyolefin resins with, for example, maleic acid. The modified polyolefin resin used as the second material exhibits a high bonding strength to the third material. Further, the third material is selected from the group consisting of polyamide resins such as 6-nylon, 6,6-nylon and 11-nylon; and polyester resins such as polyethylene terephthalate, polybutylene terephthalate and a blend polymer containing at least one of these polymer.

DESCRIPTION OF PREFERRED EMBODIMENTS

Figure 1:
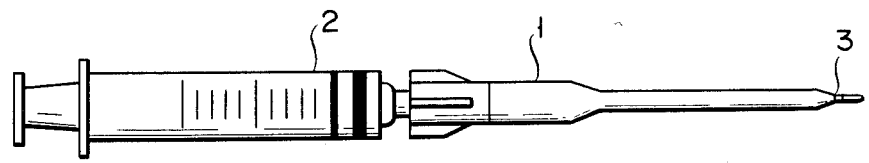
FIGS. 1-3 collectively show how to use a guiding tube for rod-like medical instruments.

As seen from FIGS. 4-7, a guiding tube 11, for medical instruments according to one embodiment of the present invention comprises a main body 13 formed of a mixture of the first and second materials and a stripe 14 formed of a third material. The main body 13 is substantially in the shape of a hollow tube provided with a longitudinal slit 12, and the stripe 14 is embedded in the slit 12 of the main body 13. The guiding tube 11, which comprises large and small diameter portions, is formed in a single step by contour extrusion.

Polyolefin resins such as a high-density polyethylene, polypropylene and ethylene-propylene copolymer are used as the first material as noted above. The second material should be capable of forming a polymer blend with the first material and should exhibit a high bonding strength to the third material. Specifically, the second material should have a bonding strength high enough to prevent the stripe from being detached from the main body and, thus, to prevent blood leakage or the like during insertion of the guiding tube into a living body. The second material meeting these requirements is prepared by modifying polyolefin resins with, for example, maleic acid. It is desirable to prepare the second material by modifying the polymer used as the first material.

The third material should be substantially incapable of bonding with the first material such that the bonding strength with the second material should be weakened to enable the stripe to be detached from the main body by application of a predetermined force after use of the guiding tube. Of course, the third material should exhibit a high bonding strength with the second material. The third material meeting these requirements includes polyamide resins, such as 6-nylon, 6,6-nylon and 11-nylon, and polyester resins, such as polyethylene terephthalate, polybutylene terephthalate, and a polymer blend containing at least one of these polymers. Incidentally, it is desirable to use synthetic resins as the first to third materials because synthetic resins facilitate the molding operation used in manufacturing the guiding tube. However, it is possible to use other materials as long as the requirements described above are satisfied.

The bonding strength between the main body 13 and the stripe 14 of the guiding tube 11 depends on the type of the second material as well as on the mixing ratio of the second material to the first material. It follows that it is possible to control the bonding strength between the main body 13 and the stripe 14 as desired by properly selecting the type and mixing ratio of the second material noted above in view of the shape and thickness of the main body and the stripe. Suppose the main body 13 is formed of a mixture of a polyolefin resin used as the first material and a maleic acid-modified polyolefin resin used as the second material, with the stripe 14 being formed of a polyamide resin or a polyester resin used as the third material. In this case, the mixing ratio of the first material to the second material should range between 10:1 and 2:1, preferably, between 6:1 and 3:1.

Figure 5:
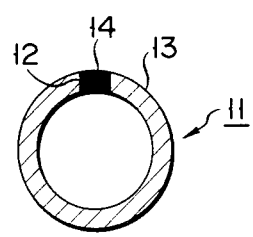
FIG. 5 is a cross-sectional view along line II—II of FIG. 4.
Figure 8:
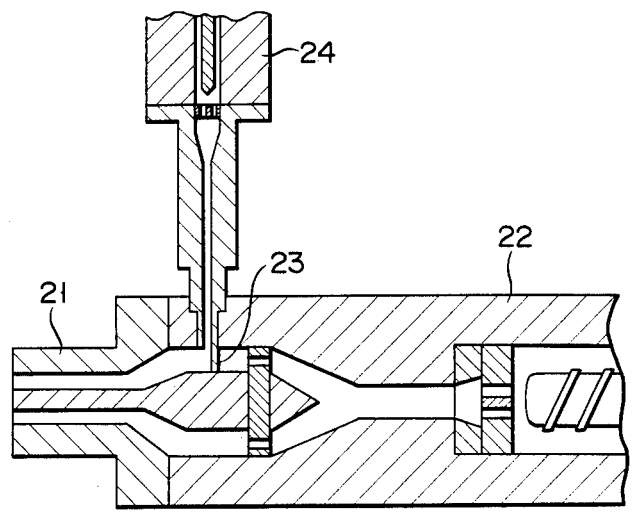
FIG. 8 is a cross-sectional view exemplifying an apparatus used for manufacturing a guiding tube for a medical instrument of the present invention.

FIG. 8 shows an extruder used for manufacturing the guiding tube 11 for medical instruments. It is seen that the extruder comprises a first extruding section 22 provided with an annular die 21 at the tip and a second extruding section 24 provided with a nozzle 23 open in the molten resin passageway upstream of the die 21. These first and second extruding sections (22, 24) are operated simultaneously, with the result that the guiding tube 11 having the stripe 14 embedded in the slit 12 of the main body 13 as shown in FIG. 5 is extruded through the die 21. It should be noted that the cross-sectional shape of the stripe 14 conforms with the cross-sectional shape of the nozzle 23, making it possible to optionally select the cross-sectional shape of the stripe 14.

Figure 2:
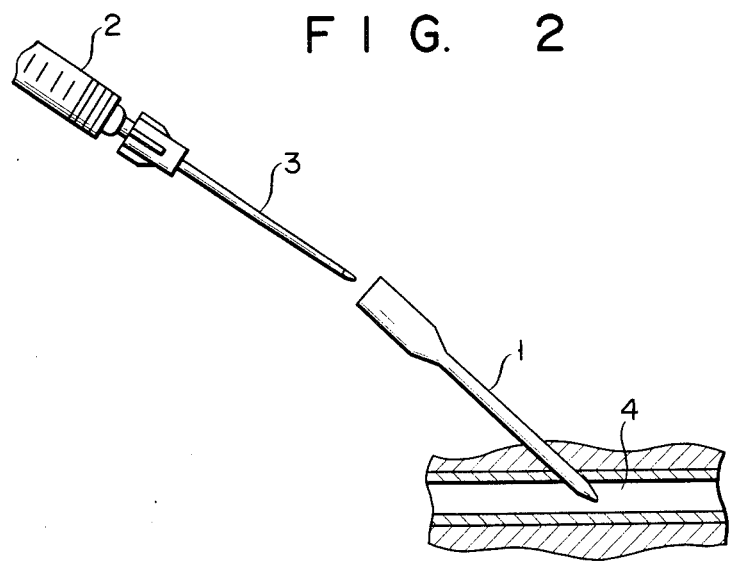
Figure 3:
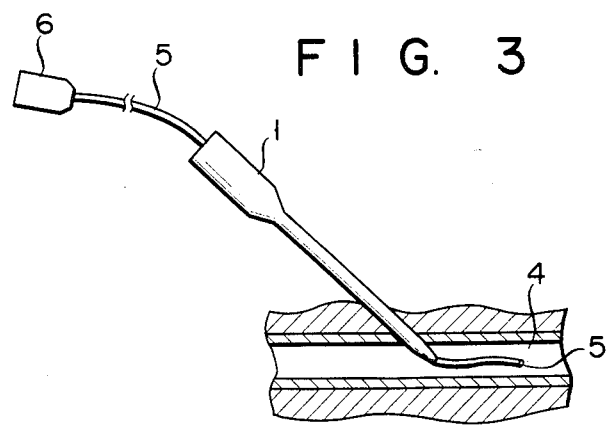
Figure 4:
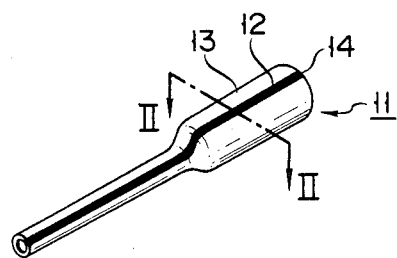
FIG. 4 is an oblique view showing a guiding tube for medical instruments according to one embodiment of the present invention.

The guiding tube 11 of the present invention is used substantially as shown in FIGS. 1 to 3. In the first step, the guiding tube 11 is mounted to a syringe as shown in FIG. 1 and, then, inserted into, for example, a blood vessel together with the inner needle of the syringe. After the guiding tube 11 has been secured to the blood vessel, the inner needle of the syringe is withdrawn from the guiding tube 11, followed by inserting, for example, a catheter into the blood vessel through the guiding tube.

Figure 6:
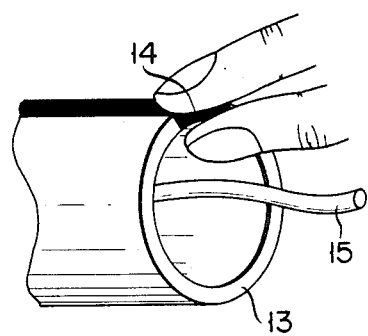
FIGS. 6 and 7 are oblique views, each showing how the guiding tube is removed from a medical instrument after use.
Figure 7:
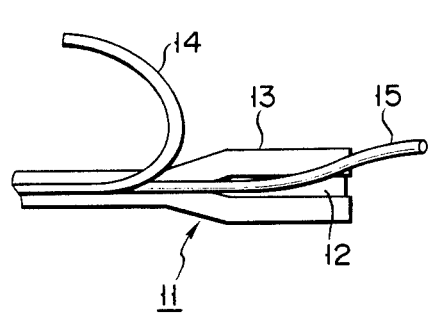

After the catheter has been secured to the blood vessel as desired, the guiding tube 11 is removed from the catheter. In removing the guiding tube 11, the stripe 14 is pulled outward, as shown in FIG. 6, with the result that the stripe 14 is removed so as to expose the slit 12 of the main body 13, as shown in FIG. 7. Naturally, the exposed slit 12 permits the guiding tube 11 to be readily removed from the catheter 15.

Figure 9:
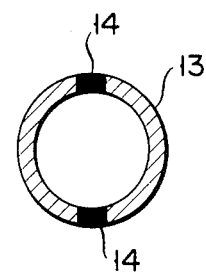
FIG. 9 is a cross-sectional view showing a modification of the guiding tube of the present invention.

In the embodiment described above, the guiding tube 11 is used for guiding a catheter. However, it is possible to use the guiding tube of the present invention for guiding any kind of rod-like medical instrument. Also, the guiding tube 11 comprises a single stripe 14 in the embodiment described above. However, it is also possible to provide a plurality of stripes 14 as shown in FIG. 9. Further, the relationship in width between the width of main body 13 and the stripe 14 is not restricted to that shown in the drawings and can be determined, as desired.

EXAMPLE 1

A guiding tube fitting a 16G inner needle was prepared by extrusion molding using an extruder as shown in FIG. 8. The main body of the guiding tube was formed of a polymer blend consisting of 4 parts by weight of polypropylene as a first material and 1 part by weight of Modik P-300 F (trade name of maleic acid-modified polypropylene manufactured by Mitsubishi Petrochemical Co., Ltd.) as a second material. On the other hand, the stripe was formed of 6-nylon (third material). The guiding tube was found to be free of problems such as cracking of the tip portion in the after-treatment applied to the tip portion with the 16G inner needle held therein. Also, the tip portion of the guiding tube was free from roughening, cracking, etc. when the guiding tube was stuck in a blood vessel of a dog together with the inner needle. Further, the stripe was readily peeled from the main body after removing the guiding tube.

Control 1

A guiding tube was prepared by extrusion molding as in Example 1. In this case, the main body of the guiding tube was formed of polypropylene, with the stripe being formed of polyethylene. The guiding tube was found to be free of problems such as cracking of the tip portion in post extrusion treatments of the tip portion to enable the tip portion to fit a 16G inner needle. However, it was impossible to remove the stripe from the main body.

Control 2

A guiding tube was prepared as in Example 1, except that the main body and stripe of the guiding tube were formed of polypropylene and polyvinyl chloride, respectively. The stripe readily peeled from the main body when cutting the guiding tube, making post treatment of the guiding tube impossible.

EXAMPLE 2

A guiding tube fitting a 16G inner needle was prepared by extrusion molding using an extruder as shown in FIG. 8. The main body of the guiding tube was formed of a polymer blend consisting of 4 parts by weight of polypropylene as a first material and 1 part by weight of Modik P-300F as a second material. The stripe was formed of a polymer blend (third material) consisting of 1 parts by weight of 6-nylon and 1 parts by weight of 6,6-nylon. The guiding tube was found to be free of problems, such as cracking of the tip portion during post treatment of the tip portion with the 16G inner needle held therein. Also, the tip portion of the guiding tube was free from roughening, cracking, etc. problem when the guiding tube was stuck in a blood vessel of a dog together with the inner needle. Further, the stripe was readily peeled from the main body allowing removal of the guiding tube.

As described above in detail, the guiding tube of the present invention comprises a main body provided with a longitudinal slit and a stripe embedded in the slit of the main body. The main body is formed of a mixture of first and second materials, with the stripe being formed of a third material. It is important to note that the first material is substantially incapable of bonding to the third material. On the other hand, the second material exhibits a high bonding strength to the third material. It follows that it is possible to optimally control the bonding strength between the main body and the stripe by properly selecting the mixing ratio between the first and second materials. Naturally, cracking or the like during post treatment of the guiding tube or during transport of the product guiding tube are highly unlikely. Of course, blood leakage can be prevented during insertion of, for example, a catheter through the guiding tube. What should also be noted is that the guiding tube can be manufactured in a single step by contour extrusion, leading to low manufacturing costs for the guiding tube.

What is claimed is:

1. A tube for guiding rod-like medical instruments into a living body, comprising:
   a main body provided with a longitudinal slit and formed of a mixture of first and second materials; and
   a stripe embedded liquid-tight in the slit of the main body and formed of a third material;
   said first material being substantially incapable of bonding to the third material, and said second material exhibiting a high bonding to the third material such that the stripe can be readily detached from the slit by application of a predetermined force to allow the guiding tube to be removed from the medical instrument after introduction of the medical instrument through the guiding tube.

2. The tube for guiding rod-like medical instruments according to claim 1, wherein the first material is a polyolefin resin.

3. The tube for guiding rod-like medical instruments according to claim 1, wherein the second material is a polyolefin resin modified to exhibit a high bonding strength to the third material.

4. The tube for guiding rod-like medical instruments according to claim 1, wherein the third material is selected from the group consisting of polyamide resin and polyester resin.

5. The tube for guiding rod-like medical instruments according to claim 1, wherein the second material is a polyolefin resin modified with maleic acid.

6. The tube for guiding rod-like medical instruments according to claim 1, wherein the first material is a polyamide resin, the second material is a modified polyolefin resin, and the third material is a polyester resin.

7. The tube for guiding rod-like medical instruments according to claim 1, wherein the second material is a polymer prepared by modifying the polymer used as the first material.

8. The tube for guiding rod-like medical instruments according to claim 1, wherein the first material is a polyolefin resin, the second material is a modified polyolefin resin, and the third material is polyamide resin or polyester resin.

9. The tube for guiding rod-like medical instruments according to claim 7, wherein the second material is a polyolefin resin modified with maleic acid.

10. The tube for guiding rod-like medical instruments according to claim 4, wherein the third material is selected from the group consisting of 6-nylon, 6,6-nylon, 11-nylon, polyethylene terephthalate, polybutylene terephthalate and a polymer blend containing at least one of these polymers.

11. A tube for guiding rod-like medical instruments according to claim 1, wherein the second material is capable of forming a polymer blend with the first material.

12. A medical instrument-guiding assembly, comprising:
   (i) a tube for guiding rod-like medical instruments into a living body, comprising: a main body provided with a longitudinal slit and formed of a mixture of first and second materials; and
   a stripe embedded liquid-tight in the slit of the main body and formed of a third material; said first material being substantially incapable of bonding to the third material, and said second material exhibiting a high bonding to the third material such that the stripe can be readily detached from the slit by application of a predetermined force to allow the guiding tube to be removed from the medical instrument after introduction of the medical instrument through the guiding tube; and
   (ii) an inner needle provided with a hub engaged with the proximal end of the guiding tube and detachably inserted into the guiding tube, the blade tip portion of the inner needle projecting through the distal end of the guiding tube.

* * * * *